(12) United States Patent
Porret et al.

(10) Patent No.: US 8,056,719 B2
(45) Date of Patent: Nov. 15, 2011

(54) MULTIPURPOSE PACKAGES FOR STERILE PRODUCTS OR PRODUCTS TO BE STERILIZED

(75) Inventors: Jean-Yves Porret, Gieres (FR); Hubert Jansen, Stolberg (DE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 2005 days.

(21) Appl. No.: 10/485,931

(22) PCT Filed: Nov. 16, 2001

(86) PCT No.: PCT/FR01/03612
§ 371 (c)(1),
(2), (4) Date: Aug. 27, 2009

(87) PCT Pub. No.: WO02/40063
PCT Pub. Date: May 23, 2002

(65) Prior Publication Data
US 2010/0270197 A1  Oct. 28, 2010

(30) Foreign Application Priority Data

Nov. 20, 2000 (FR) ..................................... 00 14977

(51) Int. Cl.
*A61B 17/06* (2006.01)
*B65D 83/10* (2006.01)
(52) U.S. Cl. ..................... 206/439; 206/370; 206/459.1; 422/22; 422/26; 422/300

(58) Field of Classification Search .......... 206/363–370, 206/438, 439, 571, 572, 484.2, 459.1; 220/377; 422/22–27, 291–300
See application file for complete search history.

(56) References Cited

U.S. PATENT DOCUMENTS

| 4,884,694 | A | * | 12/1989 | Sengewald | 206/439 |
| 5,342,673 | A | * | 8/1994 | Bowman et al. | 206/438 |
| 5,830,547 | A | * | 11/1998 | MacKenzie et al. | 206/439 |
| 6,164,044 | A | * | 12/2000 | Porfano et al. | 422/28 |
| 6,629,602 | B1 | * | 10/2003 | Heyman | 206/438 |

* cited by examiner

*Primary Examiner* — Luan K Bui
(74) *Attorney, Agent, or Firm* — Hoffmann & Baron, LLP

(57) ABSTRACT

The invention concerns a package (2) for sterilized products or products to be sterilized comprising a plastic box (4) and a lid (16) fixed on the box (4) to seal the latter with a tight sealing zone. The invention is characterized in that the lid (16) comprises: a plastic cover sheet (20) transparent for electronic irradiation and for light radiation; at least a window (22) provided in the cover sheet (20); at least a sheet of selectively sealing material (24) integral with said cover sheet (20) and closing the window (22); and an opaque screen (26, 126) for at least an electronic irradiation passing through the cover sheet or the selectively sealing material, said screen extending inside the package (2), proximate to the cover sheet (20), so as to allow through a sterilizing gas, for example ethylene oxide (ETO) or water vapor, through the selectively sealing material (24).

18 Claims, 2 Drawing Sheets

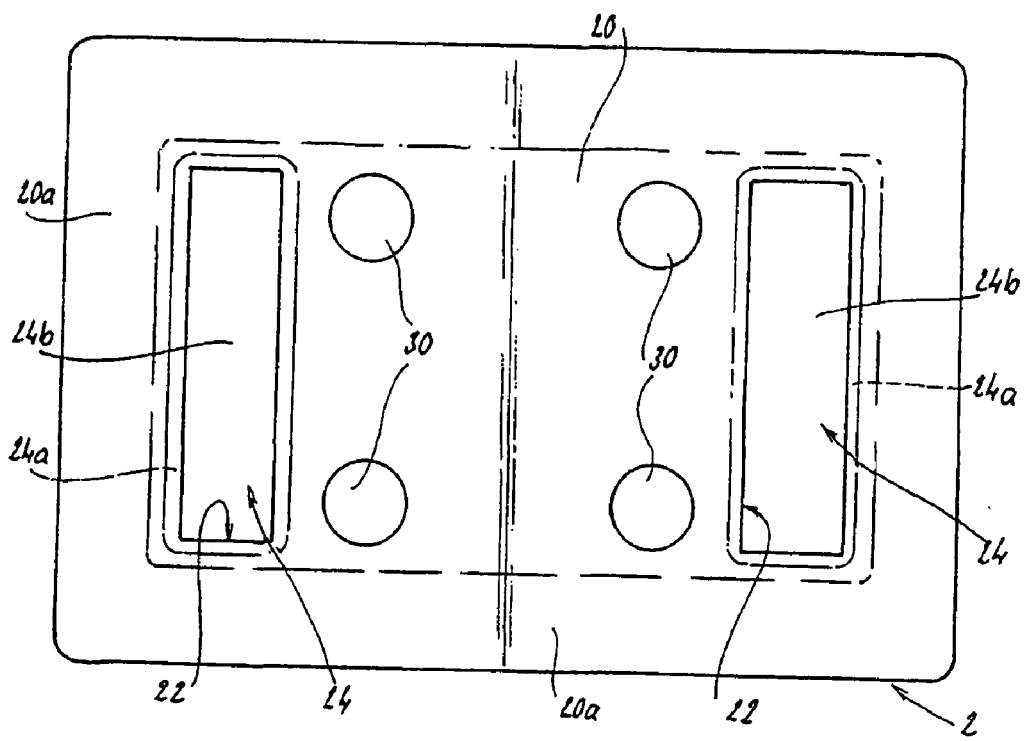
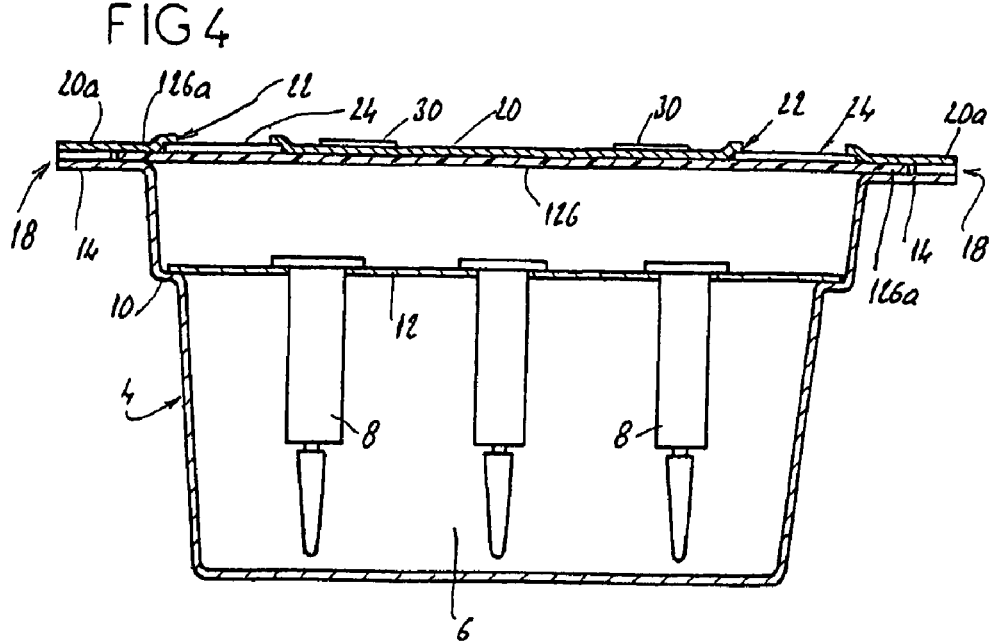

MULTIPURPOSE PACKAGES FOR STERILE PRODUCTS OR PRODUCTS TO BE STERILIZED

The present invention relates to the field of sterile or sterilized packaging, and more particularly to packaging intended to transport sterilized products or products intended to be sterilized.

The conditions of sterility in which certain stages of the handling or transportation of products or instruments intended for medical use are to be performed are extremely strict, particularly in the pharmaceutical industry. It is therefore extremely important to produce packaging compatible with such requirements.

In the remainder of the description, mention will be made of a certain number of expressions, which we need to define below.

The expression "selectively impervious", as, used in the present description and in the claims, is to be understood as meaning that the material is designed, in terms of structure, to control any exchange between the inside of the packaging and its external environment. This means, among other things, that the packaging is impervious, individually or in combination, to contamination by micro-organisms, bacteria and/or a biologically active material likely to come into contact with the packaging while it is being handled, while at the same time remaining permeable to a sterilization or decontamination gas, for example of the ethylene oxide type or a high-temperature sterilizing or decontaminating fluid, for example steam up to 130° C., more generally 120° to 127° C. and preferably between 121° and 123° C.

The expression "high temperature" is also and more generally to be understood as meaning temperatures close to the temperatures at which the plastics materials present deform.

The expressions "plastic" and "plastics material" are to be understood as meaning any material chosen from the polymer families such as styrenes, acrylics, polysulphones, polycarbonates, polyesters, polyolefins, etc. including copolymers and polymer combinations and alloys. The "plastic" is, for example, polystyrene, polyethylene or polypropylene.

Mention will also be made of a "screen against electron irradiation", which is to be understood as including a material capable of partially or fully reflecting and/or absorbing the kinetic energy of the electrons from a beam and therefore of slowing these electrons down or even preventing them from passing through the said material.

The expression "screen against light radiation" is to be understood as defining a material capable of reflecting, attenuating or preventing light radiation, for example pulsed or ultraviolet, from passing through it.

The terms "transparent" and "opaque" are to be considered with respect to electron radiation on the one hand and with respect to light radiation on the other hand. A material is transparent if light radiation or electrons can pass through it when it is subjected to electron irradiation. A material is therefore opaque to electron irradiation or to light radiation if it is capable of reflecting, attenuating and/or absorbing the kinetic energy of the electrons or if it prevents light radiation from passing through it. The opacity and/or transparency of a material are usually determined by parameters such as the thickness, density and coefficient of reflection or of attenuation.

Packaging for sterile products or products intended to be sterilized with a gas of the ethylene oxide type and comprising a tub made of plastic and a cover made of selectively impervious material allowing the said tub to be sealed with an impervious sealing zone are known.

Certain types of packaging such as those used for transporting syringes before they are filled with an active product or drug are currently transported in plastic boxes, for example made of polystyrene, covered with a cover sheet made of a selectively impervious material. The latter is, for example, a sheet based on filaments of HDPE (high density polyethylene) or some other polymer, bound together especially by heat and pressure. A product such as this is marketed, for example, under the trade mark TYVEK®.

Products intended to be sterilized are thus placed inside a tub, which is then sealed with the selectively impervious sheet. A sterilization fluid then enters the tub through the sheet of selectively impervious material. The tub containing the sterilized products is then placed in a protective bag so that it can be transported. Another method consists in first of all placing the tub in the bag equipped with a selectively impervious zone, and then sterilizing it.

By way of example, a tub or packaging such as this may contain syringes intended to be filled with a drug in a sterile room or controlled-environment room. Before the said syringes are filled, the protective bag needs to be opened and the packaging, which may be contaminated, needs to be decontaminated before it is taken, for example, into a sterile room. Such decontamination can be achieved using an electron beam developing enough energy that when it has passed through the cover sheet (selectively impervious material) it delivers a dose of irradiation of, for example, 25 kGy. This means that it can be taken that the selectively impervious material has been decontaminated throughout its thickness, particularly in the sealed zone at the interface between the tub and the said selectively impervious material.

This type of decontamination using an electron beam may, however, exhibit drawbacks. This is because the electrons that may pass through the sheet of selectively impervious material carry the risk, on the one hand, of altering or adversely affecting the material of which the syringes or products placed in the tub are made, for example glass and, on the other hand, of using the oxygen in the air contained in the said tub to generate ozone. The latter may adversely affect rubber elements or components such as the caps of needles mounted on syringes, for example, or may pollute the atmosphere. Filling the syringes with a drug in an environment containing ozone may also be unadvisable.

The use of decontamination using light radiation is also not advisable because the said light radiation is not able to pass through the sheet of selectively impervious material when the latter is opaque to light, which is generally the case, and is therefore not able to reach a zone located at the interface between the cover and the tub. This zone, for example containing a layer of adhesive, may exhibit irregularities and it is therefore essential that these irregularities which may be contaminated be reached with a decontamination means.

Furthermore, it is to be noted that sterilization using a high-temperature sterilizing or decontaminating fluid, for example steam at 121° C., causes stress in the materials present, in this instance the material known as TYVEK® and that of the tub; given the relatively large size of the tubs and packagings, this gives rise to tension in the means of connection between the said sheet of selectively impervious material and the peripheral edge of the tub. These tensions may give rise to deformation of the tub and/or detachment between the sheet of selectively impervious material and the said tub.

Other agents for sterilization via a gaseous route are, for example, vapours or plasmas of hydrogen peroxide, formaldehyde, glutaraldehyde, peracetic acid, chlorine dioxide, ozone, etc.

The drawbacks of these sterilizing agents are associated with the difficulty of controlling the said vapours or plasmas, with the toxic and harmful nature of certain agents and/or residues, and with their incompatibility with certain materials.

Sterilization by electromagnetic radiation, for example microwave sterilization, is also known. The same type of packaging as the one used for gaseous sterilization is then used, this being so as to allow gaseous exchanges between the external surroundings and the interior volume of the tub. These exchanges are needed because of the thermal expansions of the atmosphere inside the tub, associated with temperature variations and rises.

The object of the present invention is to produce packaging for products intended to be sterilized, by any type of sterilization, and in particular sterilization with ethylene oxide (ETO) or using a high-temperature sterilizing, fluid, the said packaging also being capable of being externally decontaminated using various types of decontamination and, in particular, using an electron beam, pulsed light or ultraviolet radiation.

Another object of the present invention is to produce packaging for products intended to be sterilized, which packaging is capable of indicating what type of sterilization and decontamination it has been subjected to.

An additional object of the present invention is to produce packaging which imperviously seals a tub containing products intended to be sterilized using a sterilizing fluid of the steam or ethylene oxide type while reducing as far as possible the amount of time needed for such a sterilizing operation.

The objects of the present invention are achieved using packaging for sterile products or products intended to be sterilized comprising a tub made of plastic and a cover fixed to the tub so as to seal the latter in a selectively impervious manner.

According to the invention, the cover comprises:
  a cover sheet made of plastic, transparent to electron irradiation and light radiation;
  at least one window formed in the cover sheet,
  at least one sheet of a selectively impervious material, secured to the said cover sheet and closing off the window;
  and a screen which is opaque to at least an electron irradiation passing through the cover sheet or the selectively impervious material, the said screen extending inside the packaging near the cover sheet so as to allow a sterilizing gas, for example ethylene oxide or steam, to enter through the selectively impervious material.

According to one embodiment of the packaging according to the invention, the cover comprises usage indicators making it possible to identify and indicate the type of sterilization and of decontamination to which it has been subjected.

According to one embodiment of the packaging according to the invention, the selectively impervious material has a peripheral connecting zone over which an adhesive compatible with high-temperature sterilization is discretely or continuously spread, and a central zone which remains devoid of adhesive.

The packaging according to the invention has the advantage that it can be used with several methods of sterilizing and decontaminating. The packaging can be used as it is or with predefined arrangements. It is therefore not necessary to design a special product compatible with a particular sterilization or decontamination method used.

Other features and advantages will also become apparent from the detailed description given hereinafter, given by way of example, with reference to the appended drawing, in which:

FIG. 3 depicts a view from above of the embodiment of FIG. 1;

FIG. 4 depicts another embodiment of the packaging according to the invention.

Figure 1:
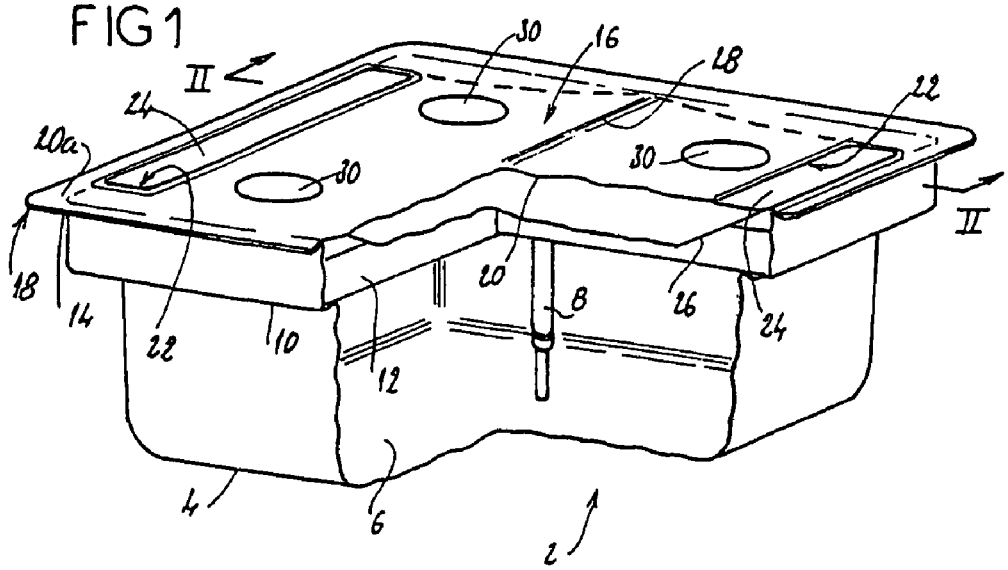
FIG. 1 depicts a perspective view with partial cutaway of one example of packaging according to the invention.

The packaging 2 according to the invention comprises a tub 4 (partially cut away in FIG. 1) delimiting an interior volume 6 intended to contain contents to be sterilized. These contents consist, for example, of syringes 8. The tub 4 has internally for this purpose a first peripheral edge 10 extending towards the outside of the tub 4 and intended to form a ledge for a support 12 for the syringes 8. This support 12 consists, for example, of a plate in which shafts or orifices are made, through which the syringes 8 pass.

The tub 4 also has an upper peripheral edge 14 which is roughly horizontal and extends towards the outside of the said tub 4. The latter is made, for example, of a plastic of the polystyrene type or of some other polymer. The material of which the tub 4 is made may be opaque, transparent or semi-transparent to light radiation, for example radiation of visible or ultraviolet type.

The packaging 2 also comprises a cover 16 fixed to the tub 4 so as to seal the latter along an impervious sealing zone. The cover 16 is, for example, bonded with its peripheral edge 16a on the upper peripheral edge 14 of the tub 4. A layer of adhesive 18 provides the interface between the peripheral edge 16a and the upper peripheral edge 14. The layer of adhesive, for example of the hot melt type 18, is chosen from adhesives that can withstand high temperatures, for example of the order of 121° C., corresponding to steam sterilization.

The cover 16 comprises a cover sheet 20 made of plastic for sealing the tub 4. The cover sheet 20 is transparent to electron irradiation and to light radiation, for example ultraviolet radiation. The opacity/density/thickness characteristics of the cover sheet 20 are therefore chosen accordingly. The cover sheet 20 has at least one window 22, obtained for example by any known means, particularly by cutting out. The cover sheet 20 depicted in the figures comprises two windows 22. Each window 22 has, for example, a longitudinal shape and extends near the upper peripheral edges 14 of the tub 4.

The cover 16 also comprises at least one sheet 24 of a selectively impervious material secured to the cover sheet 16 and closing off each of the windows 22.

The selectively impervious material 24 is, for example, a material based on filaments of HDPE (high density polyethylene) or other polymers, bound together by heat and pressure. The filaments are agglomerated in such a way as to form a microporous structure, impervious in particular to the micro-organisms or other bacteria. According to one embodiment, the selectively impervious material 24 comprises TYVEK®. The sheet 24 of selectively impervious material is, with its periphery 24a, bonded onto or preferably under the cover sheet 20. The selectively impervious material may also consist of natural fibres such as plant fibres, for example cellulose fibres, compatible with high-temperature sterilization.

The cover 16 is also associated with a screen 26 which is opaque at least to an electron irradiation passing through the cover sheet 20. This screen 26 extends into the packaging 2 near the cover sheet 20 so as to allow a sterilizing gas, for example ethylene oxide (ETO) or steam, to enter through the selectively impervious material.

The screen 26 for example comprises a flexible metal foil. The screen 26 may thus consist of a flexible aluminium foil.

Figure 2:
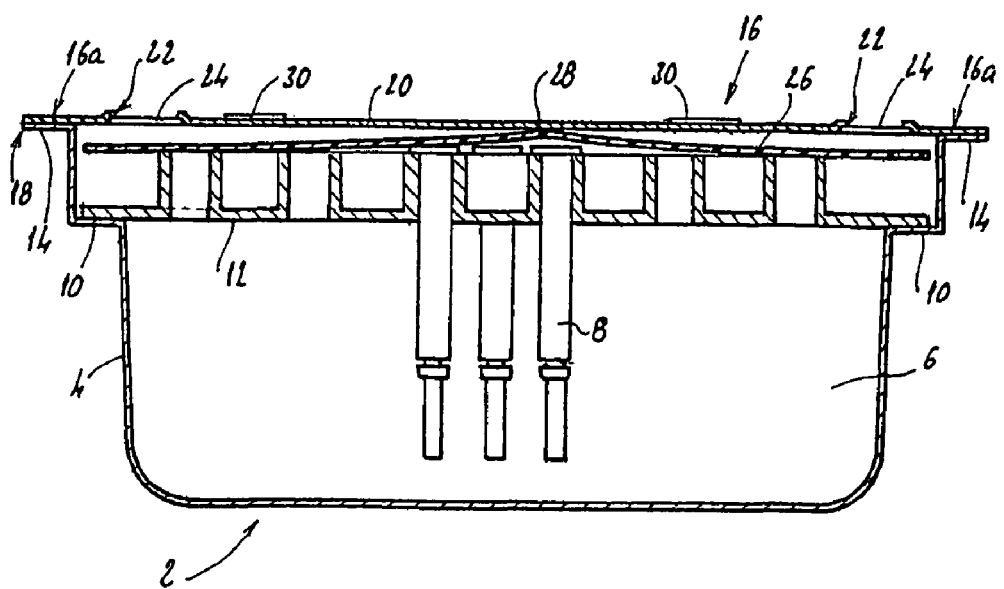
FIG. 2 depicts the embodiment of FIG. 1 in a section on II-II of FIG. 1.

In the embodiments depicted more particularly in FIGS. 1 and 2, the screen 26 is fixed under the cover sheet 20 along a fixing line 28, fixing points or a fixing zone for example near the centre of the said cover sheet 20. Any known fixing or connecting means may be envisaged for producing this fixing line 28. Fixing may, for example, be achieved by bonding, welding or goffering.

According to another embodiment according to the invention, the screen 26 for example comprises an assembly of two sheets of selectively impervious material. An assembly such as this may also be fixed on the cover sheet 20 along the fixing line 28. The position of the peripheral edge 10 and the dimensions of the support 12 are chosen so that the screen 26 which rests on the said support 12 on each side of the fixing line 28 extends in the vicinity of and under the cover sheet 20. The distance between the screen 26 and the cover sheet 20 is thus reduced as far as possible while at the same time maintaining a passage for a sterilizing gas.

Another embodiment depicted in FIG. 4 shows the screen 126 consisting, for example, of an assembly of two sheets of selectively impervious material. In this embodiment, the screen 126 extends under the cover sheet 20. The screen 126 also has dimensions which allow its peripheral part 126a to be sandwiched between the cover sheet 20 and the upper peripheral edge 14 of the tub 4. The tub 4 is sealed by the cover sheet 20 by means of the layer of adhesive 18 that provides the interface between the said cover sheet 20 and the said upper peripheral edge 14, and the screen 126 may or may not be secured to the cover sheet 20 and/or to the upper peripheral edge 14. According to another embodiment, the screen 126 is impervious. In this case the screen 126 also has orifices in fluidic communication with at least one window 22.

The cover 16 of the packaging 2 according to the invention also comprises usage indicators 30 identifying and indicating the nature of sterilization and decontamination to which the said packaging 2 has been subjected. The usage indicators 30, known per se, are, for example, indicators which change colour according to the treatment experienced. The person handling the packaging 2 therefore always knows to what kind of sterilization the syringes 8 have been subjected and to what kind of decontamination the packaging 2 has been subjected.

The cover sheet 20 is transparent to electron radiation and to light radiation. The transparency of the cover sheet 20 with respect to electron radiation and with respect to light radiation of the pulsed-light or ultraviolet-radiation type allows a zone located at the interface between the said cover sheet 20 and the upper peripheral edge 14 to be decontaminated. Irregularities in the layer of adhesive 18, which may be contaminated, can thus be contaminated by an electron beam or light radiation as mentioned before.

The tub 4 is made, for example, of a plastic transparent to light radiation. Transparency with respect to visible light radiation makes it possible to identify and to constantly check, during any decontamination operation, the contents of the packaging 2. The material of which the tub 4 is made for example has a density/thickness pairing such that it stops electrons from an irradiating electron beam. This makes it possible to avoid adversely affecting the products or contents contained in the packaging 2, in this instance the syringes 8, and to avoid the generation of ozone with the air.

The selectively impervious material preferably has a peripheral connecting zone 24a over which an adhesive compatible with high-temperature sterilization is uniformly spread, and a central zone 24b which remains devoid of adhesive. The absence of adhesive in this central zone 24b eases and accelerates the passage of a sterilization gas of the ETO type or of steam through the selectively impervious material 24. The lengths of time needed to sterilize a packaging 2 may thus be reduced.

The screen 126 extends under each window 22 so as to form a zone that is permeable to a sterilizing gas of the ETO type or steam. This gas thus passes through three layers of a selectively impervious material. Such a thickness is opaque on the one hand to light radiation and, on the other hand, to certain electron irradiations. An irradiation dose of, for example, 25 kGy after passing through the selectively impervious material that closes off the window 22 can thus be absorbed by the screen 126. Electrons can thus be prevented from entering the interior volume 6 and therefore creating ozone or adversely affecting the syringes 8.

Such a dose of electron radiation used for decontamination is also absorbed by the screen 26 (cf. FIGS. 1 and 2) whose density and/or thickness are chosen accordingly. The density/thickness pairing for the cover sheet 20 is also chosen to make the said cover sheet 20 transparent to electron irradiation and, in particular, its peripheral part 20a fixed or bonded to the upper peripheral edge 14. Light radiation, for example ultraviolet radiation, can thus decontaminate the interface connecting the said cover sheet 20 and the upper peripheral edge 14. The screen 26 (cf. FIG. 2) has, on each side of the fixing line 28, parts which are not closely connected to the cover sheet 20 and, in particular, to the selectively impervious material, so as not to impede the passage of a sterilizing gas of the ETO type or steam. This is particularly advantageous when the screen 26 is impermeable to a sterilizing gas, as is the case, for example, of an aluminium foil.

According to another embodiment of the packaging according to the invention, it is also possible, for certain materials, to replace the layer of adhesive 18 with heat sealing.

It goes without saying that the invention is not limited to the embodiment described hereinabove by way of example, but that, on the contrary, it encompasses all the alternative forms of embodiment thereof that fall within the field of protection defined by the claims appended hereto. Thus it is possible for the screen 26 to not be connected to the cover sheet at all, but simply to rest on the products contained in the packaging, on a piece contained in the packaging or on supports that the latter comprises on its inside.

The invention claimed is:

1. Packaging (2) for sterile products or products intended to be sterilized comprising a tub (4) made of plastic and a cover (16) fixed to the tub (4) so as to seal the latter with an impervious sealing zone, characterized in that the cover (16) comprises:
   a cover sheet (20) made of plastic, transparent to electron irradiation and light radiation;
   at least one window (22) formed in the cover sheet (20);
   at least one sheet (24) of a selectively impervious material, secured to the cover sheet (20) and closing off the window (22); and
   a screen (26, 126) which is opaque to at least an electron irradiation passing through the cover sheet or the selectively impervious material, the screen extending inside the packaging (2) near the cover sheet (20) so as to allow a sterilizing gas to enter through the selectively impervious material.

2. Packaging (2) according to claim 1, characterized in that the at least one sheet (24) of selectively impervious material is bonded under the cover sheet (20).

3. Packaging (2) according to claim 1, characterized in that the selectively impervious material is a material based on filaments of HDPE or some other polymer, bound together by heat and pressure.

4. Packaging (2) according to claim 3, characterized in that the selectively impervious material comprises TYVEK®.

5. Packaging (2) according to any one of claims 1 to 4, characterized in that the window (22) extends near the upper peripheral edges (14) of the tub (4).

6. Packaging (2) according to claim 1, characterized in that the screen (26, 126) comprises an assembly of two sheets of selectively impervious material.

7. Packaging (2) according to claim 1, characterized in that the screen (26, 126) comprises a metallized material or a flexible metal foil.

8. Packaging (2) according to claim 7, characterized in that the screen (26) is a flexible aluminium foil.

9. Packaging (2) according to claim 1, characterized in that the screen (26, 126) is fixed under the cover sheet (20) along a fixing line (28) or along fixing points.

10. Packaging (2) according to claim 1, characterized in that the screen (126) extends under the cover sheet (20) and has dimensions allowing its peripheral part (126a) to be sandwiched between the cover sheet (20) and the upper peripheral edge (14) of the tub (4).

11. Packaging (2) according to claim 1, characterized in that the screen (126) extends under the cover sheet (20) and has dimensions allowing its peripheral part (126a) to be sandwiched between the cover sheet (20) and the upper peripheral edge (14) of the tub (4) on the one hand, and on the other hand has orifices for fluidic communication with at least one window (22).

12. Packaging (2) according to claim 1, characterized in that the cover (16) comprises usage indicators (30) making it possible to identify and indicate the type of sterilization to which the packaging (2) has been subjected.

13. Packaging (2) according to claim 1, characterized in that the tub (4) is made of a plastic that is transparent to light radiation.

14. Packaging (2) according to claim 1, characterized in that the at least one sheet (24) of selectively impervious material has a peripheral connecting zone (24a) over which an adhesive compatible with high-temperature sterilization is continuously spread, and a central zone (24b) which remains devoid of adhesive.

15. Packaging (2) according to claim 1, characterized in that the screen (26) is not connected to the cover sheet and rests on the products contained in the packaging (2), on a piece (12) contained in the packaging or on supports that the latter comprises on its inside.

16. Packaging (2) according to claim 1, characterized in that said sterilizing gas is ethylene oxide.

17. Packaging (2) according to claim 1, characterized in that said sterilizing gas is steam.

18. Packaging (2) according to claim 1, characterized in that the cover (16) comprises usage indicators (30) making it possible to identify and indicate the type of decontamination to which the packaging (2) has been subjected.

* * * * *